United States Patent [19]
Moon

[11] Patent Number: 5,946,741
[45] Date of Patent: Sep. 7, 1999

[54] HYGIENIC, REMOVABLE TOILET ATTACHMENT FOR ENEMA, DOUCHE OR COLONIC IRRIGATION

[76] Inventor: In E. Moon, 19031 Antioch Dr., Irvine, Calif. 92715

[21] Appl. No.: 08/975,803

[22] Filed: Nov. 21, 1997

Related U.S. Application Data

[60] Provisional application No. 60/031,689, Nov. 22, 1996.

[51] Int. Cl.⁶ ........................................... A47K 3/20
[52] U.S. Cl. .................. 4/420.1; 4/420.3; 4/420.4; 4/443; 4/448; 604/275; 604/276
[58] Field of Search ................. 4/420.1, 420.2, 4/420.3, 420.4, 443, 447, 448; 604/275, 278, 279, 276

[56] References Cited

U.S. PATENT DOCUMENTS

| | | |
|---|---|---|
| 1,838,356 | 12/1931 | Berry . |
| 1,992,132 | 2/1935 | Spicher . |
| 2,007,069 | 7/1935 | Berg ........................................ 604/276 |
| 2,528,095 | 10/1950 | Ward . |
| 2,583,298 | 1/1952 | Kowan ................... 604/276 |
| 4,205,402 | 6/1980 | Miller .......................... 4/448 |
| 4,696,673 | 9/1987 | Ledin-Bonevik . |
| 4,764,997 | 8/1988 | Anderson et al. ....................... 4/420.4 |
| 5,138,726 | 8/1992 | Campbell . |
| 5,274,856 | 1/1994 | Bernard et al. . |

FOREIGN PATENT DOCUMENTS

| | | |
|---|---|---|
| 576051 | 12/1993 | European Pat. Off. ............... 604/279 |
| 424749 | 2/1935 | United Kingdom . |
| WO 85/04331 | 10/1985 | WIPO . |
| 0 274 415 | 1/1988 | WIPO . |
| WO 94/25087 | 11/1994 | WIPO . |

OTHER PUBLICATIONS

PCT International Search Report, dated Nov. 20, 1998, pp. 1–4.

*Primary Examiner*—Henry J. Recla
*Assistant Examiner*—Tuan Nguyen
*Attorney, Agent, or Firm*—Knobbe, Martens, Olson & Bear, LLP

[57] ABSTRACT

A toilet attachment is configured for positioning between a toilet seat and a toiled bowl. In use, the toilet attachment is secured by the weight of the toilet seat. The toilet attachment has a base plate and a tubular irrigation assembly which can be connected to a fluid line. The base plate has an upper and lower surface, a rear end and a front end. When the base plate is installed, the rear end faces a rear portion of the bowl and the front end faces a front portion of the bowl. The base plate has ports to receive and secure the fluid line and the irrigation assembly. These ports are located at the front end. The irrigation assembly comprises an irrigation tip, and in one embodiment of the toilet attachment, a restictor as a limiter for preventing insertion of the tip too far into a body cavity.

20 Claims, 5 Drawing Sheets

HYGIENIC, REMOVABLE TOILET ATTACHMENT FOR ENEMA, DOUCHE OR COLONIC IRRIGATION

This application claims the benefit of U.S. Provisional application Ser. No. 60/031,689 filed Nov. 22, 1996.

FIELD OF THE INVENTION

The present invention relates to a toilet attachment for enema, douche or colonic irrigation, and more particularly to a toilet attachment that can be removed fast and easily and allows hygienic use. The present method further relates to a method for applying such a toilet attachment.

BACKGROUND OF THE INVENTION

Colonic irrigation is used to remove the plaster-like fecal coating that sometimes forms on the walls of the colon. In such cases enemas are not effective to dissolve the coating. Furthermore, to remove this coating too rapidly would cause the inner lining of the colon to become "raw" and painful. For removal, the fecal coating in the colon must be thoroughly soaked and saturated with water so that its removal can take place gradually and comfortably. This gradual removal can be accomplished by a series of colon irrigations in which many gallons of water, several ounces at a time, are introduced into the colon through the rectum. The water is expelled after each introduction, requiring an apparatus to contain the expelled liquid until it can be safely discarded, or requiring apparatus to guide the expelled water into a disposal container. This apparatus is expensive, bulky and awkward to use in a home environment, especially as home colonic equipment often includes boards on which a person lies in a reclined position during the irrigation. Further, the volume of water involved makes it difficult to perform colonic irrigation in the home while remaining clean.

Additionally, if the irrigating tube is inserted improperly into the rectum, the irrigation may be ineffective, or harmful. The rectal tip of the irrigation device should never go into the rectum over 2.5 to 3 inches. Colon perforation, sepsis and possible injury of the anal canal of rectum may result with a misdirected or inadequately lubricated tip.

Further, enemas also introduce water into the colon through the rectum, although the volume of water used is much less. As enemas are preferably performed while lying on a person's side, with the water being expelled while sitting, cleanliness and convenience are typically compromised. Thus, the same or similar concerns on cleanliness, convenience and safety exist. Likewise, for a douche water is also introduced into a body cavity in small amounts, yet similar concerns exist as to the safety, convenience and cleanliness There is thus a need for a simple irrigation device that may be used safely and cleanly to irrigate body cavities in the home.

SUMMARY OF THE INVENTION

An aspect of the invention involves a toilet attachment that can be positioned between a toilet seat and a toilet bowl and can be connected to a fluid line. The toilet attachment comprises a tubular irrigation assembly and a base plate. The base plate has an upper and lower surface, a rear end and a front end. When installed, the rear end faces a rear portion of the bowl and the front end faces a front portion of the bowl. The base plate has ports to receive and secure the fluid line and the irrigation assembly. At least one of these ports is located at the front end. The toilet attachment can easily be attached to and removed from a toilet to store the toilet attachment when it is not in use. The irrigation assembly and the fluid line can be removed from the base plate, which allows easy cleaning and replacement of parts that get into contact with a user's body and/or a user's fluids or excrements.

A further aspect of the invention involves a toilet attachment having a safety feature. The toilet attachment comprises an irrigation assembly with an irrigation tip and a means for preventing insertion of the irrigation tip into a user's body cavity beyond a predetermined distance. This means is disposed on the assembly at a preset distance from the tip. The means may have a variety of shapes, e.g., a double "L" shape, a lateral "U" shape, or a lateral "S" shape. The means is sized to prevent easy or unintentionally insertion into a rectum or vagina. The various embodiments of the safety feature further adds flexibility to the irrigation assembly to allow a user more mobility and provide for more comfort than a hard tube.

Another aspect of the invention involves a toilet attachment comprising an L shaped tube to be attached to a base plate which can be positioned between a toilet seat and a toilet bowl. The L shaped tube is to be connected to a fluid line. The toilet attachment further comprises a tubular irrigation assembly having an irrigation tip and a generally U shaped form, and a means for preventing insertion of the irrigation tip too far into a user's body cavity as described above. The L shaped tube has a first end to connect to the fluid line, and a second end to receive a connecting end of the irrigation assembly. The base plate has an upper and lower surface, a rear end and a front end. When installed, the rear end faces a rear portion of the bowl and the front end faces a front portion of the bowl. The base plate has a hole in proximity to the front end to receive a portion of the L shaped tube, and brackets attached on the upper surface of the base plate to secure the tube. The irrigation assembly is connected to the portion of the tube that is fed through the hole. The L shaped tube can be easily removed from and attached to the flat base plate making the attachment particularly portable.

A still further aspect of the invention involves a method for applying a toilet attachment for irrigating a body cavity. The method places a support between a toilet bowl and a toilet seat to hold a fluid connector, and removably connects a fluid source to one end of the fluid connector. The method further removably connects an irrigation assembly to the fluid connector so fluid from the source can flow to the irrigation tip, and provides the irrigation tip with at least one portion that changes the direction of the fluid flow by at least 90°. One portion is located not more than about three inches from a distal end of the irrigation tip to limit insertion of the tip into a user's body cavity.

Another aspect of the invention involves an irrigation assembly suitable for a toilet attachment. The assembly comprises a tubular body having a first and second end. The first end is open, and can be removable attached to a base plate of the toilet attachment so that fluid can be fed to the assembly. The assembly further comprises an irrigation tip and a means for limiting insertion of the tip. The tip is positioned at the second end of the tubular body, and the means is disposed on the tubular body at a preset distance from the irrigation tip for limiting insertion of the tip into a user's body to a preset maximum distance. The irrigation assembly is removable attachable to the base plate so that various users may use the same base plate and change only the irrigation assembly which is partly inserted into a body cavity.

BRIEF DESCRIPTION OF THE DRAWINGS

The above-mentioned and other features of the invention will now be described with reference to the drawings of preferred embodiments of the toilet attachment. The illustrated embodiments are intended to illustrate, but not to limit the invention. In the drawings, same components have been identified by same reference numerals. The drawings contain the following figures.

DETAILED DESCRIPTION OF THE PREFERRED EMBODIMENT

Figure 1:
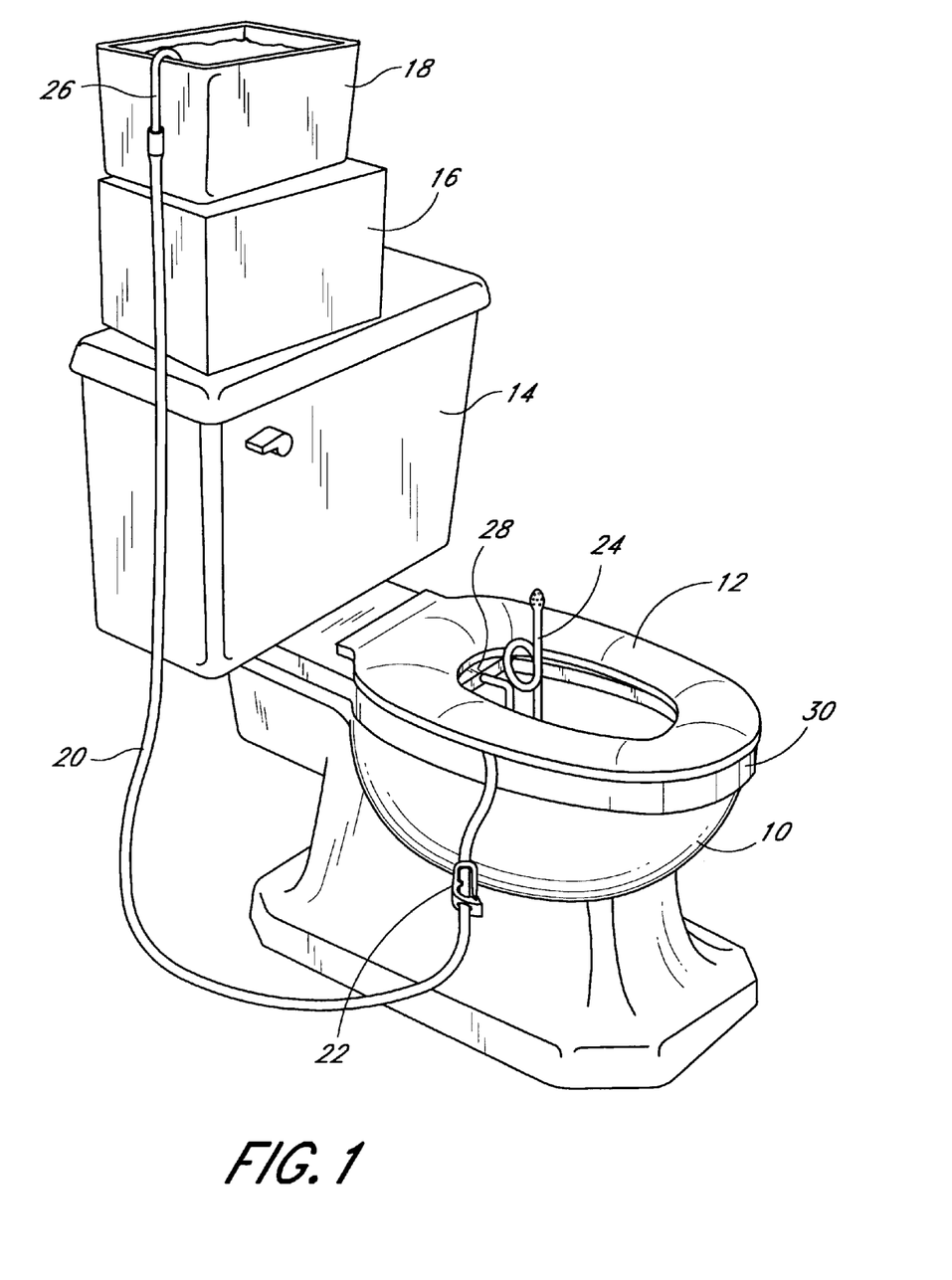
FIG. 1 is an overview of a toilet comprising an installed a toilet attachment in accordance with one embodiment of the present invention attached to it.

FIG. 1 shows an overview of a conventional toilet with an installed toilet attachment for enema, douche or colonic. The toilet comprises a toilet bowl 10 and a water reservoir 14 in water communication with the toilet bowl 10 for flushing the toilet bowl 10 after use. A toilet seat 12 is attached to the toilet bowl 10 in a conventional hinged manner. The toilet attachment is positioned between the toilet seat 12 and a rim 30 of the toilet bowl 10, and comprises a base plate 28 (only partly visible in FIG. 1), a tubular irrigation assembly 24 and a fluid line 20.

The fluid line 20 provides for fluid communication between a fluid reservoir 18 and the irrigation assembly 24, subsequently referred to as the rectal assembly, which may be partly inserted into the rectum or vagina for use. Preferably the fluid reservoir 18 is placed at an elevated location so that gravity determines the fluid pressure. In a bathroom of a private home, the elevated location can be achieved by simply placing the fluid reservoir 18 on top of the water reservoir 14, and as needed, on top of an additional support 16. The height of support 16 can be varied to adjust the gravity controlled fluid pressure through the fluid line 20. The fluid reservoir 18 may also be a bag which can be attached to a wall or ceiling by means of a hook. The location of the hook and bag can again adjust the fluid pressure. Such a bag, e.g., is used for camping or other outdoor activities to store water. A U-shaped tube 26 connects the fluid line 20 to the fluid reservoir 18. A clamp 22 is disposed on the fluid line 20 and allows the flow of fluid to be manually controlled, with the clamp 22 preferably being resiliently urged into a closed or no-flow position.

The fluid may be water or an aqueous solution comprising, e.g., a therapeutical composition. The fluid may be heated within the fluid reservoir 18 or may be filled into the fluid reservoir 18 at room or body temperature.

The fluid line 20 can be an one-piece line or a line comprising two or more interconnected pieces. Preferably, the fluid line 20 is made of a flexible material, e.g., a conventional hose. If the fluid line 20 comprises two or more pieces different materials may be used having differing flexibilities as appropriate to the use of each piece.

As an alternative to the fluid reservoir 18, the fluid line 20 can be attached to a faucet. In this case, a suitable connector is attached to the fluid line 20 to ensure a reliable water tight connection. For safety reasons, a pressure regulator is required when the fluid line 20 is connected to a faucet.

Figure 2A:
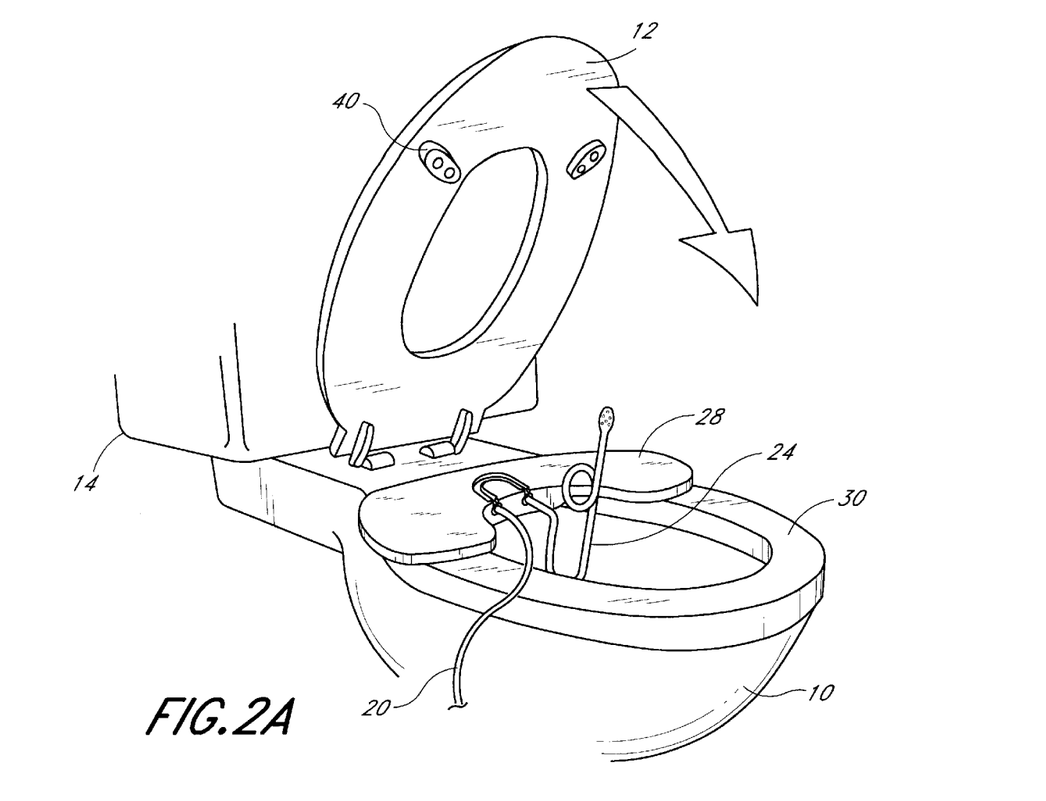
FIG. 2A is a schematic illustration of the toilet attachment positioned on top of a toilet bowl.

FIG. 2A is a schematic illustration of the toilet attachment positioned on top of a toilet bowl. The toilet seat 12 is lifted to allow a better view of the toilet attachment positioned on top of the bowl's rim 30 at the back of the bowl 10 towards the water reservoir 14. FIG. 2A also allows a better view of the rectal assembly 24 which will be described in more detail in connection with FIG. 2B and FIGS. 4A–4F.

The base plate 28 of the toilet attachment is secured to the toilet by being located between the toilet seat 12 and the bowl 10, and by having a depending portion 29 (FIGS. 2B and 3) depending into the bowl 10 and configured to rest against the curve of the bowl 10. As no further attachment means are required, the base plate 28 and its depending portion 29 are therefore the whole toilet attachment. The attachment can be easily installed and removed, e.g., for cleaning to ensure hygienic conditions. The shape of base plate 28 is advantageously adapted to the contour of the rim 30 at the back of the bowl 10 and does not significantly extend from underneath the toilet seat 12. In the illustrated embodiment of the base plate 28, the base plate 28 has a flat, curved form. The opening of the toilet bowl 10 is therefore only minimally reduced when the base plate 28 is installed. The base plate 28 has a rear end that, when installed, faces the water reservoir 14, and a front end that, when installed, faces the front of the toilet bowl 10.

Figure 2B:
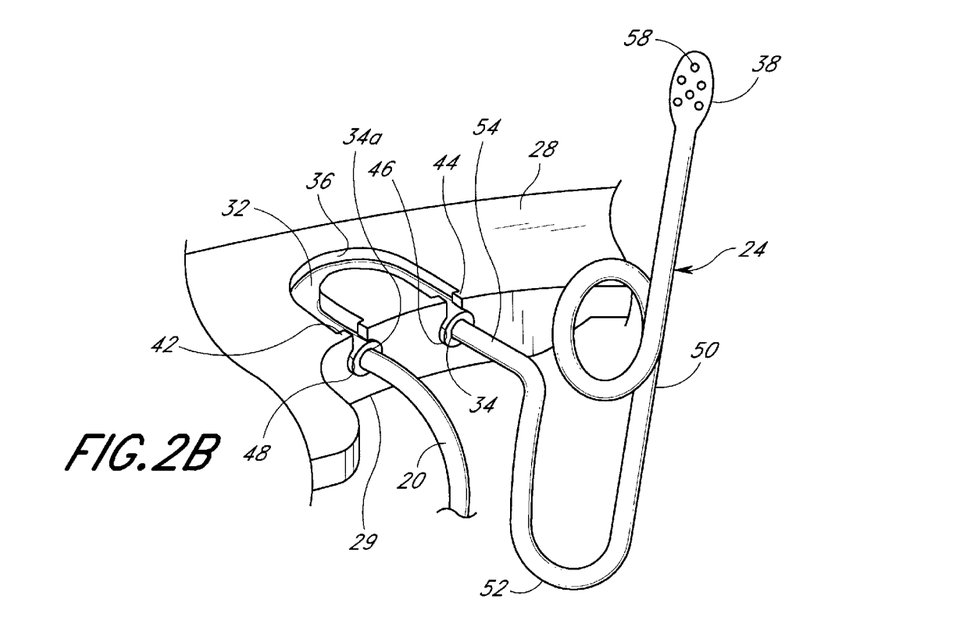
FIG. 2B is a magnified portion of a base plate of the toilet attachment and a rectal assembly.

Except for the depending portion 29 that extends inside the rim 30 of the bowl 10, the base plate 28 has a thickness that is about equal to a distance between the rim 30 and the toilet seat 12 when the toilet seat 12 is lowered. This distance is determined by the height of spacers 40 usually attached to a toilet seat 12. If the thickness is about equal to, or very slightly greater than this distance, then the weight of a user sitting on the seat 12 will trap the base plate 28 between the rim 30 and seat 12 to help hold the base plate 28 in position.

The base plate 28 holds the rectal assembly 24 in a substantially vertical position and provides for a reliable connection between the rectal assembly 24 and the fluid line 20. Preferably, the fluid line 20 and the rectal assembly 24 are both attached to the front end of the base plate 28 within the depending section of the base plate 28. In another embodiment (not shown) of the attachment, the fluid line 20 may be attached to the rear end of the base plate 28. As noted above, the depending portion 29 may be thicker than remaining portions of the base plate 28, which have to fit between the rim 30 and the toilet seat 12. The fluid line 20 is also positioned between the rim 30 and the toilet seat 12 without being significantly compressed so as to restrict fluid flow through the line 20.

FIG. 2B shows a magnified portion of a base plate 28 and a rectal assembly 24 to illustrate an example for attaching the fluid line 20 and the rectal assembly 24 to the base plate 28. In a plane parallel to an upper surface of the base plate 28, the upper surface facing the toilet seat 12, the base plate 28 has a channel or groove 36 with two ends or ports 46, 48. The channel 36 extends in the plane parallel to the upper surface. In the illustrated embodiment of the base plate 28, the channel 36 is open at the upper surface and forms a U-shaped groove 36 opening onto the upper surface of base plate 28 to allow the insertion of tube 32 having an annular cross section. Within the base plate's dependent section 29, the ends 46, 48 face the front end of the base plate 28. The groove 36 receives a flexible tube 32 which is preferably secured in a press-fit manner to allow easy removal from the base plate 28, e.g., for cleaning or replacement of the tube 32 or the base plate 28. To assist securing the tube 32, the groove ends 46, 48 comprise projections 42, 44 to narrow the diameter of the groove 36 to slightly compress the tube 32 and hold it in position while not unduly restricting flow through the tube 32. An end portion of the fluid line 20 is removably inserted into an end 34a of the tube 32, with at least one of these ends being sufficiently resilient to provide a water tight connection. Inserting parts 20, 54 into the ends 34, 34a also makes a tighter fit between the ends 34, 34a and the adjacent projections 42, 44 to further hold the tube 32 to the base plate 28.

The tubular rectal assembly 24 comprises an irrigation (rectal) tip 38, a U-shaped portion 52 and a connecting portion 50 that connects the rectal tip 38 and one end of the U-shaped portion 52. The other end of the U-shaped portion 52 is connected, at right angles to the connecting portion 50, to an end portion 54. The end portion 54 of the rectal assembly 24 is removably inserted inside an end 34 of the tube 32, with at least the end 34 or the end portion 54 being sufficiently resilient to provide a water tight connection.

The rectal tip 38 contains a plurality of holes or apertures 58 through which a fluid, such as water, flows. These holes 58 may have a diameter of about 3/32 inch and are uniformly distributed over an end portion of the connecting portion 50, this end portion forms the rectal tip 38. The rectal tip 38 may have a diameter that is equal to the diameter of the connecting portion 50. In a further embodiment of the rectal assembly 24, the tip 38 may have an enlarged bulbous shape especially suitable for a douche and for insertion into the vagina.

In a further example for attaching the fluid line 20 to the base plate 28, an end portion of the fluid line 20 may be inserted directly into the groove 36. In this case, the groove 36 and the fluid line 20 have suitable diameters to secure the fluid line 20 in the described press-fit manner. Also, the inner diameter of the fluid line 20 and the outer diameter of the rectal assembly 24 are sized and shaped to each other to provide a releasable but water tight connection.

Figure 3:
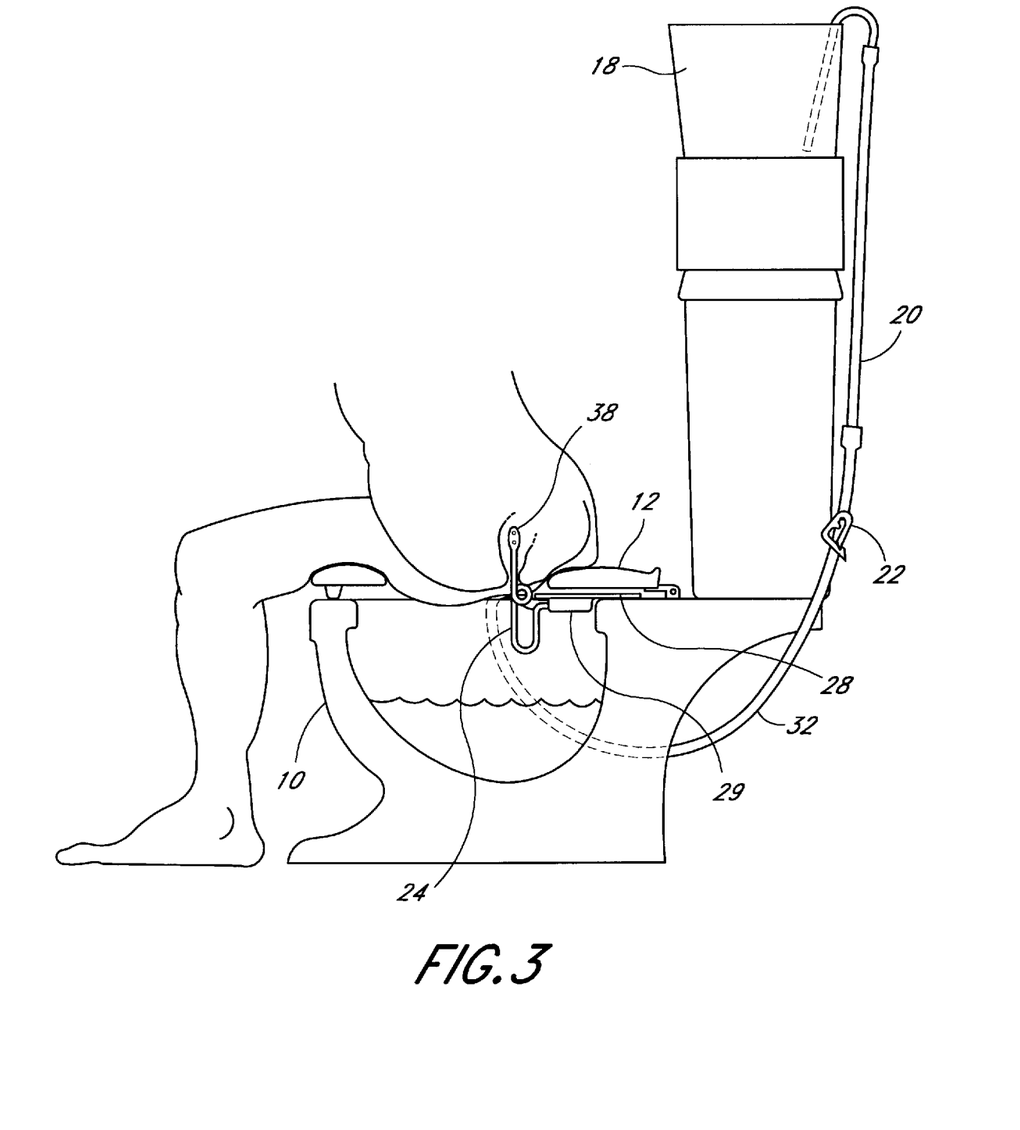
FIG. 3 schematically illustrates the use of the toilet attachment.

FIG. 3 schematically illustrates, by means of a side view of the toilet shown in FIG. 1, the use of the toilet attachment. In use, part of the rectal assembly 24 including the rectal tip 38 is inserted into a user's body. As noted above, the toilet attachment is positioned between the toilet seat 12 and the toilet bowl 10, and secured by the weight of the user, the location of the toilet attachment, and the shape of the toilet attachment. The clamp 22 is located at a suitable location on the fluid line 20 to allow convenient manual control of the fluid flow from the fluid reservoir 18 to the rectal tip 38.

If the rectal tip 38 is inserted improperly into the rectum, the irrigation may be ineffective, or harmful. The rectal tip 38 should typically not go into the rectum over about 2.5 to 3 inches (6.4 cm to 7.6 cm). Colon perforation, sepsis and possible injury of the anal canal or rectum may result with a misdirected or inadequately lubricated tip. There is more variability for inserting the tip 38 into other body cavities, with the distances set by prevailing health and safety parameters.

To guard against inserting the rectal tip 38 too far into the user's body, an insertion limiter 56 is added to the rectal assembly 24 as a safety feature. FIGS. 4A–4F show various embodiments of rectal assemblies having such a limiter 56. Each limiter 56 provides a form of projection or restraint that limits insertion of the rectal tip 38 too far into the user's body. These projections or restraints can take a variety of forms as illustrated in FIGS. 4A–4F. As the body hits these projections or restraints, the insertion of the rectal tip 38 into the body is stopped. In most cases, the limiter 56 is formed by the shape of the connecting portion 50.

Thus, the projections or restraints are preferably positioned relative to the tip 38 to limit the insertion of the tip 38 into the appropriate body cavity, with the insertion distance limited by limiter 56. In some cases, it may be desirable to vary these distances. While the previously stated lengths are preferred for the colonic application, shorter or longer dimensions may be suitable depending on the specific use of the irrigation apparatus and the person involved.

The U-shaped portion 52 of the rectal assembly 24 (FIG. 2B) provides some flexibility and thus alleviates the force with which the tip 38 is inserted into the rectum or other body cavity. The flexibility of the rectal assembly 24 made of a flexible tube enables the user to have more mobility and therefore is more comfortable than a hard tube (made of rigid plastic or stainless steel, for example). The various illustrated embodiments of the limiter 56 can be formed during or after manufacture, e.g., through thermal forming the connecting portion 50 into the desired shape. The tubular connecting portion 50 is advantageously a polyethylene tube 1/4 inch O.D., 0.170 I.D. The connecting portion 50 preferably has a diameter that is as small as possible to provide comfort, but large enough to allow sufficient fluid flow.

The limiter 56, basically, is an obstacle which, besides the illustrated embodiments, could also be a wire attached to the connecting portion 50. The limiter 56 protects a user so that the tip 38 is not unintentionally or accidentally inserted too far into the body cavity. Various shapes and configurations would be suitable to prevent the rectal tip 38 from being inserted too far into the rectum or vagina. The U shaped portion 52 (FIG. 2B), the limiter 56 and the rectal tip 38 are preferable made of a single tube and together make up the rectal assembly 24.

Figure 4A:
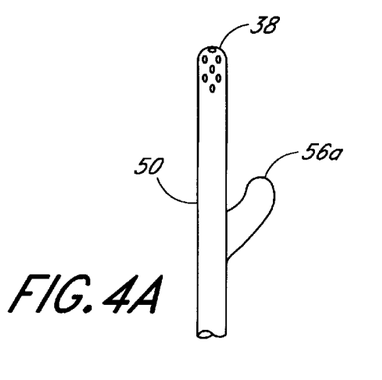
FIGS. 4A–4F various embodiments of a rectal assembly in accordance with the present invention.

FIG. 4A shows a limiter 56a comprising a plate made of 1/16 inch (0.16 cm) thick plastic plate. The plate is attached to the rectal assembly 24 at about 3 inches from the rectal tip 38. The plate can be glued or molded to the connecting portion 50 of the rectal assembly 24. The plate extends orthogonal from the portion 50 a distance sufficient to inhibit it from easily or accidentally entering a body cavity so that it limits insertion into such a body cavity.

Figure 4B:
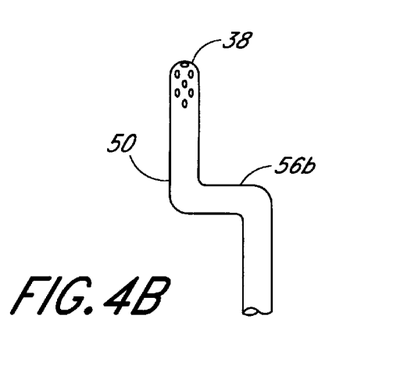

FIG. 4B shows a limiter 56b having a double "L" shape formed by laterally offsetting the tip 38 from the main portion of the connecting portion 50.

Figure 4C:
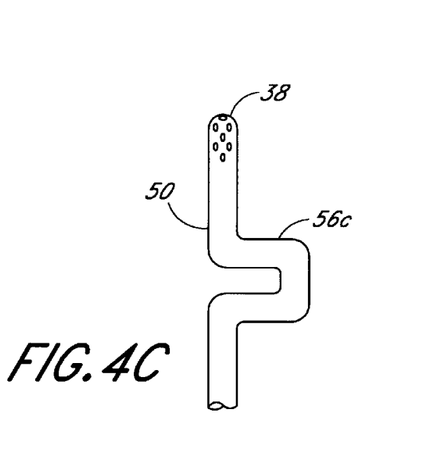

FIG. 4C shows a limiter 56c having a "C" or lateral "U" shape, which extends laterally a distance sufficient to prevent easy or accidental insertion of the limiter 56c into a body cavity.

Figure 4D:
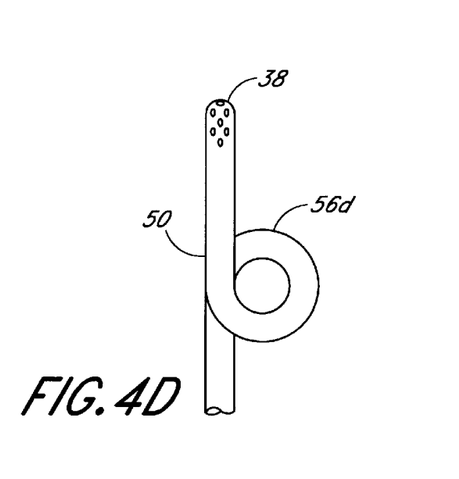

FIG. 4D shows a limiter 56d in the form of a loop formed by bending the connecting portion 50 into a loop. The loop has a sufficiently large diameter to prevent easy or unintentional insertion of the loop into a body cavity.

Figure 4E:
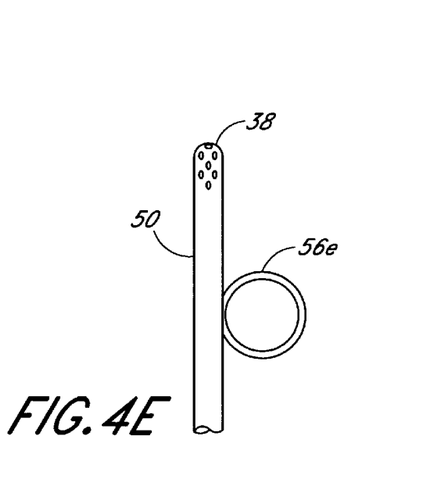

FIG. 4E shows a limiter 56e comprising a ring at about 3 inches from the rectal tip 38. The ring is made of plastic and is 3/16 inch thick and 1/2 inch in diameter. The ring's plane is parallel to the axis of the connecting portion 50. The ring has a sufficiently large diameter to prevent easy or accidental insertion of the ring into a body cavity.

Figure 4F:
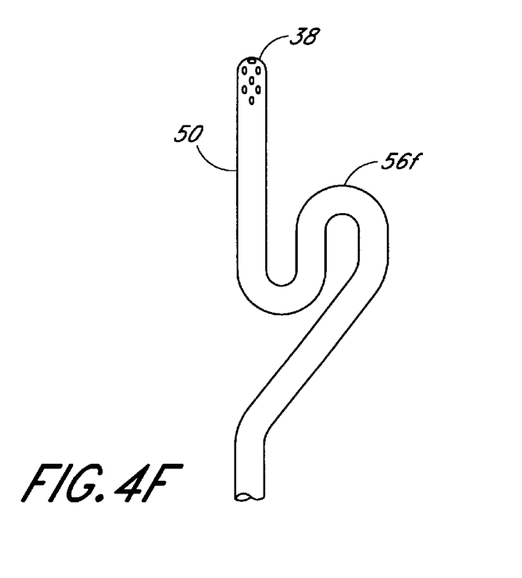

FIG. 4F shows a limiter 56f having a lateral "S" shape. The size of the "S" prevents easy or unintentional insertion of the "S" into a body cavity.

In all the above cases, the limiters 56a–56f extend laterally from the longitudinal axis of the tip 38 a distance sufficient to prevent the limiter 56 from being easily or unintentionally inserted into a rectum or vagina. For practical purposes, the limiter 56 is configured to prevent any insertion past the limiter 56. The limiter 56 is located relative to the tip 38 to permit about 2.5 to 3 inches of insertion of the tip 38, as previously discussed for colonic irrigation. The limiter 56 may be oriented to either extend toward, or face the rear or front end of the toilet. In the illustrated embodiments, the limiter 56 is placed to face the rear end of the toilet. In a further embodiment (not shown), the irrigation assembly 24 may comprise a pair of limiters 56 facing opposite directions. Further, as shown in FIGS. 4B, 4C, 4D and 4F, fluid flowing in direction to the irrigation tip 38 changes its flow direction at least once by at least 90°.

The illustrated limiters 56a–56f provide further flexibility to allow the tip 38 to gently and resiliently contact the body. The limiters 56b–56d and 56f allow the stiffness and configuration of connecting portion 50 to contribute to this increased flexibility and resilience. This reduces the force of any contact with the body to reduce the possibility of injury and to reduce the severity of any tissue injury resulting from contact with the tip 38 for prolonged time periods.

Figure 5:
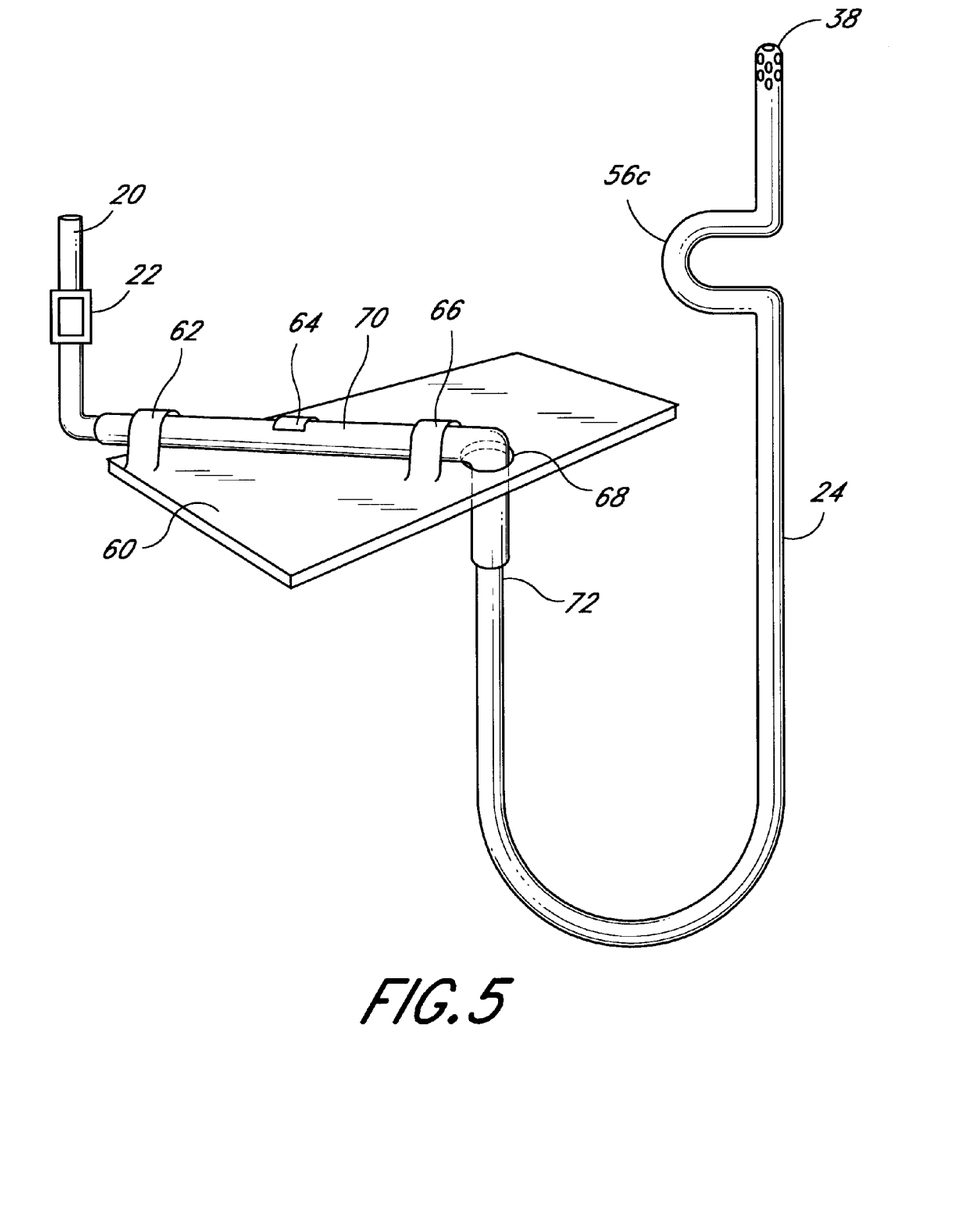
FIG. 5 is a schematic illustration of a toilet attachment in accordance with a further embodiment of the present invention.

Referring to FIG. 5, a further embodiment of a toilet attachment in accordance with the present invention is shown. An L shaped connecting base tube 70 may be stored on a flat base plate 60 when not in use and held in place by one or more resilient brackets 62, 64, 66. As described above, in use, the base plate 60 is placed over a toilet bowl, between the toilet bowl and a toilet seat toward the rear of the bowl. The base tube 70 is removed from the brackets 62, 64, 66 and the short end of the L tube 70 inserted through a hole 68 in plate 60 to hold it steady and correctly orientate that end of the tube 70. The longer end of the L tube 70 may be held in place by the brackets 62, 64, 66 which are generally C shaped with one portion extending over the tube 70. A connecting end 72 of the tubular rectal assembly 24 is inserted inside one end of the tube 70, with at least one of the tubes 70, 72 being sufficiently resilient to provide a water tight connection. Opposite the end 72 of the rectal assembly 24 is the rectal tip 38 which may be inserted into the rectum or vagina for use, as noted above. The illustrated rectal assembly 24 has a limiter 56c having the shape of a "C" (see FIG. 4C), although any of the previously described limiters 56 could be used.

The described embodiments of toilet attachments including the rectal tip may be used for enema, douche or colonic irrigation. Referring to FIG. 3, a user may advantageously lubricate the rectal tip 38 and anus, hold the rectal assembly 24 and slowly and gently insert the rectal tip 38 into the rectum as the user lowers himself or herself onto the seat 12. The rectal tip 38 should not be inserted further than the limiter (see FIGS. 4A–4F) allows, which is typically about three inches maximum. When the rectal tip 38 is properly inserted, the user opens the clamp 22 on the fluid line 32 and proceeds with the colonic irrigation.

In a further embodiment, by placing the toilet attachment in the described manner onto a conventional toilet, the toilet can be used as a bidet. In this case, the irrigation assembly may be altered to have a shorter connecting portion 50 (FIG. 2B) to position the tip 38 at an appropriate location below the rim of the seat 12.

The toilet attachment has a simple construction and elegant design that make this toilet attachment easy and safe to use, easy to carry and store, and very clean. The irrigation assembly can be made inexpensively thereby lowering the cost of the whole toilet attachment. The disposable irrigation assembly can be easily replaced to maintain hygienic conditions particularly if several persons use the same base plate. Since the irrigation assembly, the tube 32 (FIG. 2B) and the fluid line 20 can be completely removed from the base plate 28, the base plate 28 can be cleaned easily. This also allows thorough cleaning of the tube 32 and eventually of the portion of the fluid line 20 that extends into the bowl 10.

Although an exemplary embodiment of the invention has been disclosed for purposes of illustration, it will be understood that various changes, modifications and substitutions be incorporated in such embodiment without departing from the spirit of the invention as defined by the claims which follow.

What is claimed is:

1. A toilet attachment to be positioned between a toilet seat and a toilet bowl and to be connected to a fluid line, comprising:

a tubular irrigation assembly comprising a U-shaped tube having an irrigation tip defining an outlet for fluid received from the fluid line at a first end, a U-shaped portion having an inlet for receiving fluid from the fluid line at an opposite second end thereof, and a limiter disposed between said irrigation tip and said U-shaped portion at a preset distance from the outlet to limit the distance the tip is inserted into a body cavity during use and for increasing the flexibility of the insertion tip, the limiter being located along a plane passing through a longitudinal axis of the irrigation assembly; and a base plate, said base plate having an upper and lower surface, a rear end and a front end, and first and second ports in the base plate, one to receive and secure the fluid line and one to receive and secure the irrigation assembly to provide fluid for passage through the irrigation assembly, at least one of said ports being located at said front end, said base plate having at least a portion sized to fit between the toilet seat and the toilet bowl when the seat rests against the bowl.

2. The toilet attachment of claim 1, wherein the base plate further comprises a channel, said channel extending parallel to said upper surface and connecting said ports.

3. The toilet attachment of claim 2, wherein the channel is a groove having a cross section configured to hold a flexible tube and an opening at the upper surface of the base plate smaller than the diameter of the tube but large enough so the tube can be removably inserted into the channel.

4. The toilet attachment of claim 3, wherein the tube is placed in the groove and the groove receives the tube in a press-fit manner.

5. The toilet attachment of claim 3, wherein the groove contains at least one projection located in proximity to one of said ports to secure the fluid line.

6. The toilet attachment of claim 1, wherein the base plate comprises a middle and two outer sections, said middle section being thicker than said two outer sections and depending therefrom to depend into said bowl during use and about a portion of said bowl.

7. The toilet attachment of claim 1, wherein the limiter has a generally double "L" shape.

8. The toilet attachment of claim 1, wherein the limiter has a generally lateral "U", shape.

9. The toilet attachment of claim 1, wherein the limiter comprises a loop, said loop having a plane that is parallel to the tube.

10. The toilet attachment of claim 1, wherein the limiter has a generally lateral "S" shape.

11. A toilet attachment to be positioned between a toilet seat and a toilet bowl and to be connected to a fluid line, comprising:

a U-shaped tubular irrigation assembly, said irrigation assembly comprising an irrigation tip having a longitudinal axis and an outlet in fluid communication with the fluid line;

insertion limiter means disposed on said assembly for increasing the flexibility of the insertion tip and for preventing insertion of the irrigation tip into a user's body cavity beyond a preset distance, the longitudinal axis of the irrigation tip and said insertion limiter means being coplanar; and a base plate, said base plate having an upper and lower surface, a rear end and a front end, said base plate receiving and securing the fluid line and the irrigation assembly during use and sized to have at least a portion fit between the seat and bowl as the seat rests against the bowl.

12. A method for applying a toilet attachment for irrigating a body cavity, comprising the steps of:

placing a support between a toilet bowl and a toilet seat to hold a fluid connector, the support comprising a base plate having an upper and lower surface, a rear end and a front end, and first and second ports in the base plate in fluid communication with each other, at least one of said ports being located at said front end, said base plate having at least a portion sized to fit between the toilet seat and the toilet bowl when the seat rests against the bowl;

removably connecting a fluid source to one of the ports;

removably connecting a U-shaped irrigation assembly having an irrigation tip defining an outlet for fluid to the other of the ports so fluid from the source can flow to and out of the outlet of the irrigation tip;

furnishing the irrigation tip with a limiter that changes the direction of the fluid flow by at least 90°, and locating said limiter a predetermined distance from the outlet of the irrigation tip in order to limit insertion of the tip into a user's body cavity.

13. A toilet attachment for fluid irrigation of a body cavity, the attachment being for use with a toilet having a seat and bowl, comprising:

a tubular body comprising a U-shaped portion having a first end being open so that fluid can be fed through said tubular body to a second end;

an elongated irrigation tip connected to the second end of the tubular body, the tip having a longitudinal axis and holes to dispense fluid during use;

an insertion limiter extending laterally from the irrigating tip, the longitudinal axis of the irrigation tip and said insertion limiter being coplanar, said insertion limiter being disposed on the tubular body between said U-shaped portion and said second end at a preset distance from the irrigation tip to limit insertion of the tip into a user's body, said insertion limiter being adapted to increase the flexibility of the insertion tip; and a holder configured to removably connect to the tubular body and configured to have at least a portion interposed between the toilet seat and bowl when the seat rests on the bowl during use.

14. The toilet attachment of claim 13, wherein the means has a generally double "L" shape.

15. The toilet attachment of claim 13, wherein the means has a generally lateral "U" shape.

16. The toilet attachment of claim 13, wherein the means comprises a loop formed by the irrigation tip.

17. The toilet attachment of claim 13, wherein the means has a generally "S" shape.

18. A toilet attachment for use with a toilet having a seat and a bowl, to irrigate a body cavity with fluid from a fluid line, comprising:

a tubular irrigation assembly having an inlet configured to be placed in fluid communication with the fluid line and having an outlet, the irrigation assembly having a U-shaped portion and an insertion limiter disposed on said assembly at a preset distance from the outlet to hinder inserting the outlet more than said preset distance into a body cavity, the limiter extending laterally from the irrigating tip, the longitudinal axis of the irrigation tip and said insertion limiter being coplanar, said insertion limiter being adapted to increase the flexibility of the insertion tip; and a base plate sized to fit between the toilet seat and the toilet bowl when the seat rests against the bowl, the irrigation assembly being secured to the base plate during use of the toilet attachment, the tubular irrigation assembly having at least one bend in the tube intermediate the base plate and the limiter to reduce the stiffness of the tubular irrigation assembly.

19. A toilet attachment as defined in claim 18, wherein the limiter comprises a shaped tube that changes the flow of fluid to the outlet by more than 90°.

20. A toilet attachment to be positioned between a toilet seat and a toilet bowl and to be connected to a fluid line, comprising:

a tubular irrigation assembly, said assembly having an outlet for fluid received from the fluid line, the irrigation assembly having a limiter disposed on said tube at a preset distance from the irrigation tip to prevent a user from inserting the tip more than said preset distance into a body cavity, the limiter comprising a loop having a plane that is parallel to the tube, the irrigation assembly having a U-shaped tube, said tube having a first and second end, said first end comprising an irritation tip; and a base plate having an upper and lower surface, a rear end and a front end, and ports to receive and secure the fluid line and the irrigation assembly, at least one of said ports being located at said front end, and said second end of said tube being adapted to connect to one of the port.

* * * * *